(12) United States Patent
Ding et al.

(10) Patent No.: US 8,538,519 B2
(45) Date of Patent: Sep. 17, 2013

(54) METHOD AND SYSTEM FOR TREATMENT OF MECHANICAL CARDIAC ASYNCHRONY

(75) Inventors: Jiang Ding, Maplewood, MN (US); Yinghong Yu, Shoreview, MN (US); Milton M. Morris, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 2513 days.

(21) Appl. No.: 11/113,827

(22) Filed: Apr. 25, 2005

(65) Prior Publication Data

US 2006/0241703 A1 Oct. 26, 2006

(51) Int. Cl.
*A61N 1/365* (2006.01)

(52) U.S. Cl.
USPC .................................. 607/9; 607/17

(58) Field of Classification Search
USPC ...................................... 607/9, 17
See application file for complete search history.

(56) References Cited

U.S. PATENT DOCUMENTS

| | | | |
|---|---|---|---|
| 4,543,963 A | 10/1985 | Gessman | |
| 5,190,035 A | 3/1993 | Salo et al. | |
| 5,527,347 A | 6/1996 | Shelton et al. | |
| 6,161,042 A | 12/2000 | Hartley et al. | |
| 6,208,901 B1 * | 3/2001 | Hartung | 607/23 |
| 6,597,951 B2 * | 7/2003 | Kadhiresan et al. | 607/9 |
| 7,203,540 B2 | 4/2007 | Ding et al. | |
| 2003/0105496 A1 * | 6/2003 | Yu et al. | 607/17 |
| 2003/0130702 A1 * | 7/2003 | Kramer et al. | 607/9 |
| 2004/0008955 A1 | 1/2004 | Patlakh et al. | |
| 2004/0078059 A1 | 4/2004 | Ding et al. | |
| 2004/0167580 A1 | 8/2004 | Mann et al. | |
| 2004/0215258 A1 | 10/2004 | Lovett et al. | |
| 2005/0137630 A1 | 6/2005 | Ding et al. | |
| 2005/0137632 A1 | 6/2005 | Ding et al. | |
| 2005/0137634 A1 | 6/2005 | Hall et al. | |
| 2007/0150013 A1 | 6/2007 | Ding et al. | |

FOREIGN PATENT DOCUMENTS

| | | |
|---|---|---|
| WO | WO-03/037428 A2 | 5/2003 |
| WO | WO-2006/115659 A1 | 11/2006 |

OTHER PUBLICATIONS

U.S. Appl. No. 10/744,237 Advisory Action mailed Oct. 18, 2006, 3 pgs.
U.S. Appl. No. 10/744,237 Final Office Action mailed Aug. 8, 2006, 7 pgs.
U.S. Appl. No. 10/744,237 Non Final Office Action mailed Feb. 23, 2006, 11 pgs.
U.S. Appl. No. 10/744,237 Notice of Allowance mailed Dec. 1, 2006, 4 pgs.
U.S. Appl. No. 10/744,237 Response filed May 23, 2006 to Non Final Office Action mailed Feb. 23, 2006, 7 pgs.
U.S. Appl. No. 10/744,237 Response filed Oct. 10, 2006 to Final Office Action mailed Aug. 8, 2006, 6 pgs.
U.S. Appl. No. 10/744,237 Preliminary Amendment filed Aug. 18, 2005, 4 pgs.
PCT Application No. PCT/US2006/010780 International Search Report and Written Opinion mailed Jul. 6, 2006, 13 pgs.

* cited by examiner

*Primary Examiner* — Christopher D Koharski
*Assistant Examiner* — Michael D Abreu
(74) *Attorney, Agent, or Firm* — Schwegman Lundberg & Woessner, P.A.

(57) ABSTRACT

A system and method for identifying patients with asynchronous ventricular contractions due to abnormal electro-mechanical coupling and computing optimal pacing parameters for restoring synchronous contractions is disclosed. Such patients may have normal intra-ventricular and inter-ventricular conduction and cannot be identified from intrinsic conduction data alone such as QRS width. Techniques for computing optimal resynchronization pacing in order to compensate for abnormal electro-mechanical coupling are also described.

13 Claims, 4 Drawing Sheets

METHOD AND SYSTEM FOR TREATMENT OF MECHANICAL CARDIAC ASYNCHRONY

RELATED APPLICATIONS

This application is related to U.S. patent application Ser. No. 10/744,237, filed on Dec. 22, 2003, now U.S. Pat. No. 7,203,540, entitled "METHOD AND SYSTEM FOR SETTING CARDIAC RESYNCHRONIZATION THERAPY PARAMETERS", the disclosure of which is hereby incorporated by reference.

FIELD OF THE INVENTION

This invention pertains to methods and apparatus for treating cardiac disease with electrical therapy.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction.

Pacing therapy can also be used in the treatment of heart failure, which refers to a clinical syndrome in which an abnormality of cardiac function causes a below normal cardiac output that can fall below a level adequate to meet the metabolic demand of peripheral tissues. When uncompensated, it usually presents as congestive heart failure due to the accompanying venous and pulmonary congestion. Heart failure can be due to a variety of etiologies with ischemic heart disease being the most common. It has been shown that some heart failure patients suffer from intraventricular and/or interventricular conduction defects (e.g., bundle branch blocks) such that their cardiac outputs can be increased by improving the synchronization of ventricular contractions with electrical stimulation. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a most common form of CRT applies stimulation pulses to both ventricles, either simultaneously or separated by a specified biventricular offset interval, and after a specified atrio-ventricular delay interval with respect to the detection of an intrinsic atrial contraction and/or an atrial pace.

SUMMARY

Described herein are a system and method for identifying patients with asynchronous ventricular contractions due to abnormal electro-mechanical coupling and computing optimal pacing parameters for restoring synchronous contractions. Such patients may have normal intra-ventricular and inter-ventricular conduction and cannot be identified from intrinsic conduction data alone such as QRS width. Techniques for computing optimal resynchronization pacing in order to compensate for abnormal electro-mechanical coupling are also described.

DETAILED DESCRIPTION

As the term is usually used, cardiac resynchronization therapy is pacing stimulation applied to one or more heart chambers in a manner that compensates for conduction delays. Ventricular resynchronization pacing is useful in treating heart failure in patients with interventricular or intraventricular conduction defects because, although not directly inotropic, resynchronization results in a more coordinated contraction of the ventricles with improved pumping efficiency and increased cardiac output. Ventricular resynchronization can be achieved in certain patients by pacing at a single unconventional site, such as the left ventricle instead of the right ventricle in patients with left ventricular conduction defects. Resynchronization pacing may also involve biventricular pacing with the paces to right and left ventricles delivered either simultaneously or sequentially, with the interval between the paces termed the biventricular offset (BVO) interval (also sometimes referred to as the LV offset (LVO) interval or VV delay). The offset interval may be zero in order to pace both ventricles simultaneously, or non-zero in order to pace the left and right ventricles sequentially. As the term is used herein, a negative BVO refers to pacing the left ventricle before the right, while a positive BVO refers to pacing the right ventricle first. In an example biventricular resynchronization pacing mode, right atrial paces and senses trigger an AVD interval which upon expiration results in a pace to one of the ventricles and which is stopped by a right ventricular sense. The contralateral ventricular pace is delivered at the specified BVO interval with respect to expiration of the AVD interval.

Cardiac resynchronization therapy is most conveniently delivered in conjunction with a bradycardia pacing mode. Bradycardia pacing modes refer to pacing algorithms used to pace the atria and/or ventricles in a manner that enforces a certain minimum heart rate. Because of the risk of inducing an arrhythmia with asynchronous pacing, most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. For example, a ventricular escape interval for pacing the ventricles can be defined between ventricular events, referred to as the cardiac cycle (CC) interval with its inverse being the lower rate limit or LRL. The CC interval is restarted with each ventricular sense or pace. In atrial tracking and AV sequential pacing modes, another ventricular escape interval is defined between atrial and ventricular events, referred to as the atrio-ventricular pacing delay interval or AVD, where a ventricular pacing pulse is delivered upon expiration of the atrio-ventricular pacing delay interval if no ventricular sense occurs before. In an atrial tracking mode, the atrio-ventricular pacing delay interval is triggered by an atrial sense and stopped by a ventricular sense or pace. An atrial escape interval can also be defined for pacing the atria either alone or in addition to pacing the ventricles. In an AV sequential pacing mode, the atrio-ventricular delay interval is triggered by an atrial pace and stopped by a ventricular sense or pace. Atrial tracking and AV sequential pacing are commonly combined so that an AVD starts with either an atrial pace or sense. When used in CRT, the AVD may be the same or different in the cases of atrial tracking and AV sequential pacing. As the term is used herein for biventricular pacing, the AVD interval refers to the interval between an atrial event (i.e., a pace or sense in one of the atria, usually the right atrium) and the first ventricular pace which pre-excites a ventricular region. The AVD interval may be the same or different depending upon whether it is initiated by an atrial sense or pace (i.e., in atrial tracking and AV sequential pacing modes, respectively), The pacing instant for the non-pre-excited ventricle is specified by the BVO interval so that it is paced at an interval AVD+BVO after the atrial event. It should be appreciated that specifying AVD and BVO intervals is the same as specifying a separate AVD interval for each ventricle, designated as AVDR for the right ventricle and AVDL for the left ventricle.

Cardiac resynchronization therapy is most commonly applied in the treatment of patients with heart failure due to left ventricular dysfunction which is either caused by or contributed to by left ventricular conduction abnormalities such as left bundle branch block. (More rarely, some patients have a right ventricular conduction deficit such as right bundle branch block and require pre-excitation of the right ventricle in order achieve synchronization of their ventricular contractions.) In patients with a left ventricular conduction deficit, the left ventricle or parts of the left ventricle contract later than normal during systole which thereby impairs pumping efficiency. In order to resynchronize ventricular contractions in such patients, pacing therapy is applied such that the left ventricle or a portion of the left ventricle is pre-excited relative to when it would become depolarized in an intrinsic contraction. The left ventricle may be pre-excited with either biventricular pacing or with left ventricular-only pacing. Although not as common, some patients have a right ventricular conduction deficit such as right bundle branch block and require pre-excitation of the right ventricle in order achieve synchronization of their ventricular contractions. It should be appreciated that the techniques described herein could also be applied to any late-contracting ventricular region, including the right ventricle.

For optimum hemodynamic performance, it is desirable to deliver ventricular pacing, whether for resynchronization pacing or conventional bradycardia pacing, in an atrial tracking and/or AV sequential pacing mode in order to maintain the function of the atria in pre-loading the ventricles (sometimes referred to atrio-ventricular synchrony). Since the objective of CRT is to improve a patient's cardiac pumping function, it is therefore normally delivered in an atrial-tracking and/or AV sequential mode and requires specification of AVD and BVO intervals which, ideally, result in the ventricles being synchronized during systole after being optimally preloaded during atrial systole. That is, both optimal inter-ventricular synchrony and optimal atrio-ventricular synchrony are achieved. In patients with intact and normally functioning AV conduction pathways, the non-pre-excited ventricle will be paced, if at all, close to the time at which that ventricle is intrinsically activated in order to achieve optimal preloading. In patients with normal AV conduction, the optimal AVD and BVO intervals are thus related to both the intrinsic atrio-ventricular interval and the amount of pre-excitation needed for one ventricle relative to the other (i.e., the extent of the ventricular conduction deficit).

Optimal pre-excitation of the left ventricle in a given patient may be obtained with biventricular pacing or with left ventricular-only pacing by pre-exciting the left ventricle with a pace delivered to the left ventricle which excites the left ventricular free wall. The desired situation is simultaneous contraction of the left ventricular free wall and ventricular septum (septum-free wall fusion). The excitation of the ventricular septum may be a result of either intrinsic activation from the AV node or a pace delivered to the right ventricle. If intrinsic AV conduction to the right ventricle is normal, intrinsic activation of the ventricular septum occurs at an interval following an atrial contraction which produces optimal preloading of the ventricles during atrial systole. Therefore, in a patient with normal intrinsic AV conduction to the right ventricle but with a left ventricular conduction deficit, the hemodynamically optimum AVD interval for pre-exciting the left ventricle is one which results in the left ventricular free wall contracting due to the pace at the same time that the ventricular septum is contracting due to intrinsic activation. This situation may be brought about by pre-exciting the left ventricle at the optimum AVD interval with either left ventricle-only or biventricular pacing. In the latter case, depending upon the implementation, the right ventricular pace scheduled to occur at the BVO interval following expiration of the AVD interval may either be inhibited by the intrinsic right ventricular activation, occur coincidently with the right ventricular activation, or occur after intrinsic right ventricular activation during the refractory period.

Figure 1:
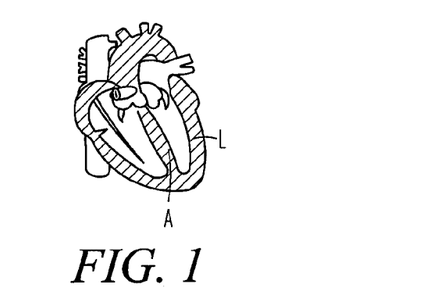
FIG. 1 is a diagram of the heart showing first and second ventricular regions.
Figure 2A:
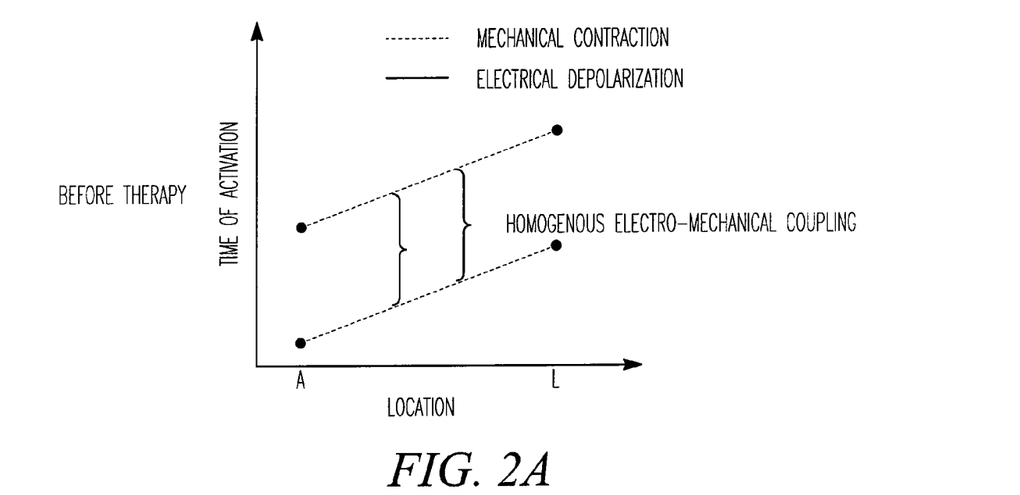
FIGS. 2A and 2B illustrate a situation where there is delayed conduction to the left ventricle.
Figure 2B:
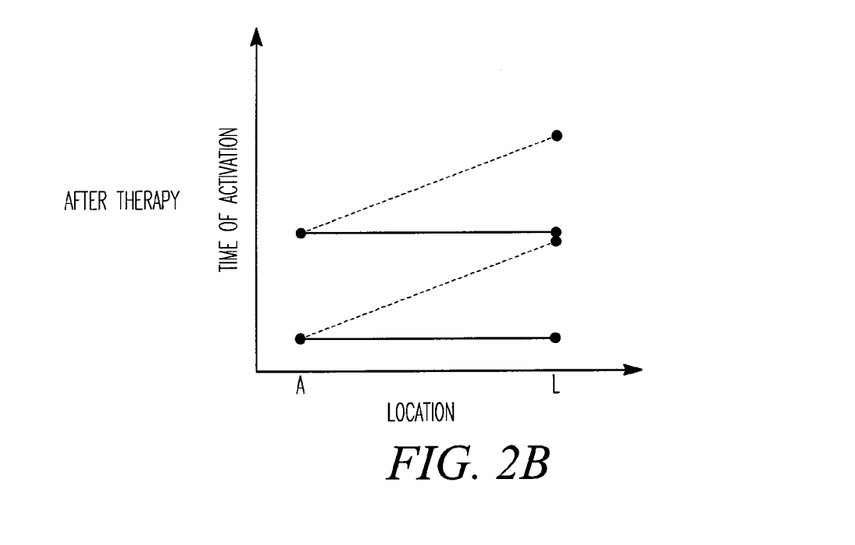

As aforesaid, CRT is most often applied in the treatment of conduction disorders affecting the left ventricle. FIG. 1 is a diagram of the heart showing a first ventricular region labeled L located in the left ventricular lateral free wall and a second ventricular location labeled A located in the ventricular septum. FIGS. 2A and 2B illustrate a typical situation where there is delayed conduction to the left ventricle. In each diagram, the mechanical and electrical activation of ventricular locations from location A to location L are plotted against the vertical axis representing time, where the activation events are labeled as MA for mechanical contraction and EA for electrical depolarization. FIG. 2A shows the sequence of events before therapy, where location A is electrically activated before location L during an intrinsic beat due to a left ventricular conduction deficit. In this example, there is homogeneous electro-mechanical coupling at each of the ventricular locations so that the mechanical delay MD between time of contraction of location A and the time of contraction L is equal to the electrical delay ED between the time of depolarization of location A and the time of depolarization of location L. The mechanical delay means that the ventricular septum contracts before the left ventricular free wall resulting in an asynchronous heart beat. CRT may be applied to compensate for this electrical delay by pre-exciting the location L with pacing pulses as illustrated in FIG. 2B. By delivering a pace to the location L at a time which results in electrical activation of location L at the same time the location A in the ventricular septum is activated by intrinsic conduction, simultaneous contraction of the locations A and L occurs which is the desired outcome. Following an atrial sense or pace, the optimum AVD interval for delivering the pace to location L is thus a function of the intrinsic atrio-ventricular delay interval to location A, designated as $IAVD_1$, and the electrical delay from location A to location L which may be expressed in terms of the intrinsic atrio-ventricular delay interval to location L, designated as $IAVD_2$. Thus, the optimum AVD interval may be computed as:

$$AVD=F(IAVD_1, IAVD_2).$$

The electrical delay from location A to location L could also be expressed in other ways such the QRS width of an electrogram or surface EKG. Methods for computing optimum AVD intervals are described in greater detail in co-pending U.S. Pat. No. 7,203,540, entitled "METHOD AND SYSTEM FOR SETTING CARDIAC RESYNCHRONIZATION THERAPY PARAMETERS".

Figure 3A:
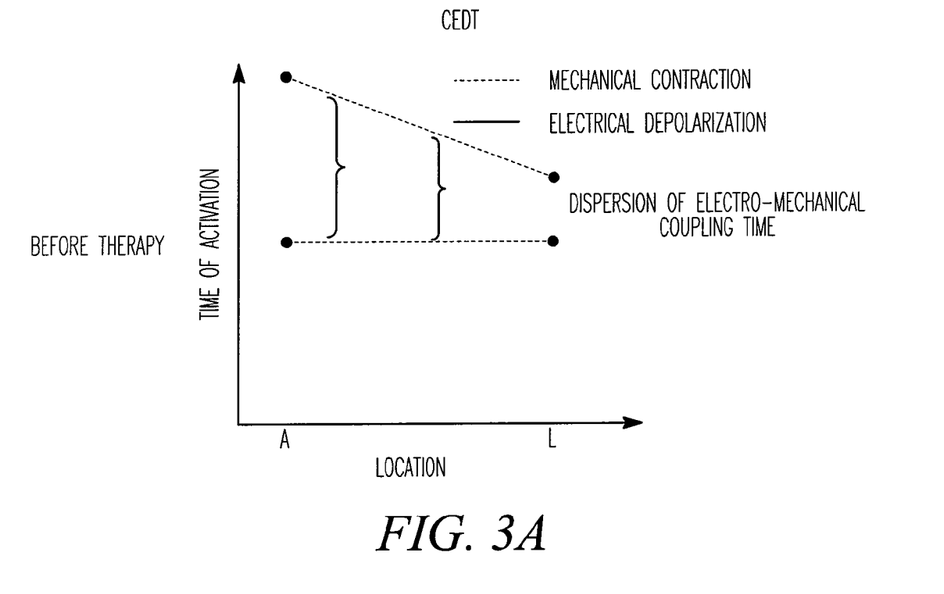
FIGS. 3A and 3B illustrate a situation where there is abnormal electro-mechanical coupling in a ventricle.
Figure 3B:
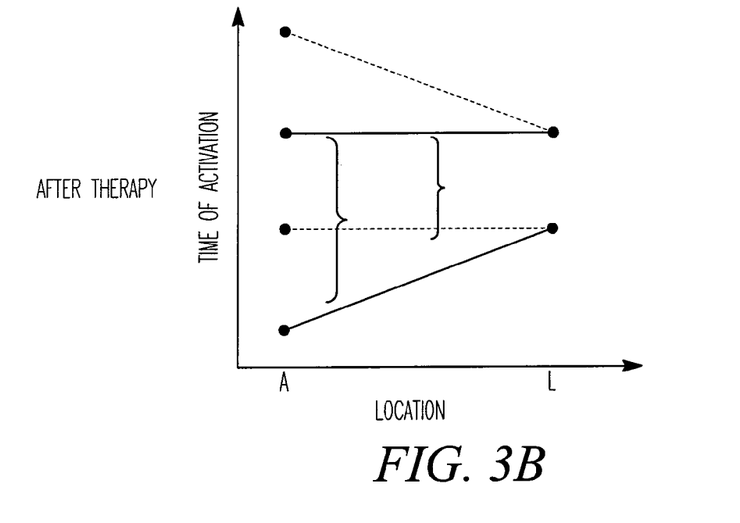

Patients who have electrical conduction delays such as illustrated by FIGS. 2A and 2B may be identified from intrinsic conduction data such as QRS width or direct measurement of electrical delays using internal electrodes. Such intrinsic conduction data can also be used to optimize CRT pacing parameters such as the AVD interval. Certain patients, however, exhibit asynchronous ventricular contractions even while their intrinsic conduction data such as QRS width is in the normal range. In these patients, there is delayed mechanical activation in a ventricular region because of abnormal electro-mechanical coupling rather than being due delays in electrical conduction. The abnormal dispersion in electro-mechanical coupling among the cardiac myocytes causes regions of the ventricle to contract at different times even while they are simultaneously electrically activated. FIG. 3A illustrates this situation in an example patient. Ventricular locations A and L are shown as being electrically activated at the same time. Due to abnormal electro-mechanical coupling, however, region A contracts later than region L to result in an asynchronous ventricular contraction. The patient may be treated with pacing therapy which introduces electrical dispersion in order to compensate for the abnormal electro-mechanical coupling as illustrated by FIG. 3B. Pre-excitation pacing of region A then causes region A to be electrically activated earlier than region L, the latter being electrically activated by intrinsic conduction. Because of the abnormal electro-mechanical coupling, however, regions A and L contract simultaneously to produce the desired synchronous contraction.

Described herein are a system and method for identifying patients with abnormal electro-mechanical coupling and computing optimal pacing parameters for restoring synchronous contractions. A scanning device is employed in order to determine the timing of mechanical activation in different ventricular regions during a cardiac cycle. The scanning device may utilize any type of scanning modality which allows for the detection of mechanical contraction in different areas of the ventricular myocardium such as echocardiography or other type of ultrasonic scanning, magnetic resonance imaging, or X-rays. In one embodiment, the scanning device detects the times at which a plurality of ventricular regions contract with reference to an atrial sense or pace and allows for the identification of an earlier contracting ventricular region and one or more later contracting ventricular regions. A sensing channel which includes an internal electrode disposed near the later contracting region and an atrial sensing channel are used to detect electrical activation of the later contracting region and atria, respectively. Another sensing channel may be employed to detect electrical activation at the earlier contracting site and determine if there is any electrical delay and its extent. Alternatively, whether a patient has an electrical conduction disorder can be determined from the QRS width of a surface EKG. The sensing channels may be part of an implantable device as described below are may be incorporated into an external device. A processing device (e.g., an external programmer or the controller of an implantable device) receives the sensing data and measures an intrinsic atrio-ventricular delay (IAVD) as the time between an atrial sense or pace and intrinsic electrical activation of the later contracting ventricular region. The processing device also receives scanning data generated by the scanning device and is configured to compute a mechanical delay (MD) as the difference between the times at which the earlier and later ventricular regions mechanically contract during a cardiac cycle.

From this information, the processing device can compute an optimal AVD for delivering resynchronization therapy in order to compensate for the electro-mechanical dispersion.

Described below is an exemplary implantable device which may be used with an external programmer and a scanning device to determine if a patient has ventricular asynchrony due to abnormal electro-mechanical coupling. The device may also be configured to deliver appropriate resynchronization pacing which disperses electrical activation of selected ventricular regions in order to compensate for the abnormal electro-mechanical coupling. An exemplary implementation scheme is also described.

1. Exemplary Hardware Platform

Figure 4:
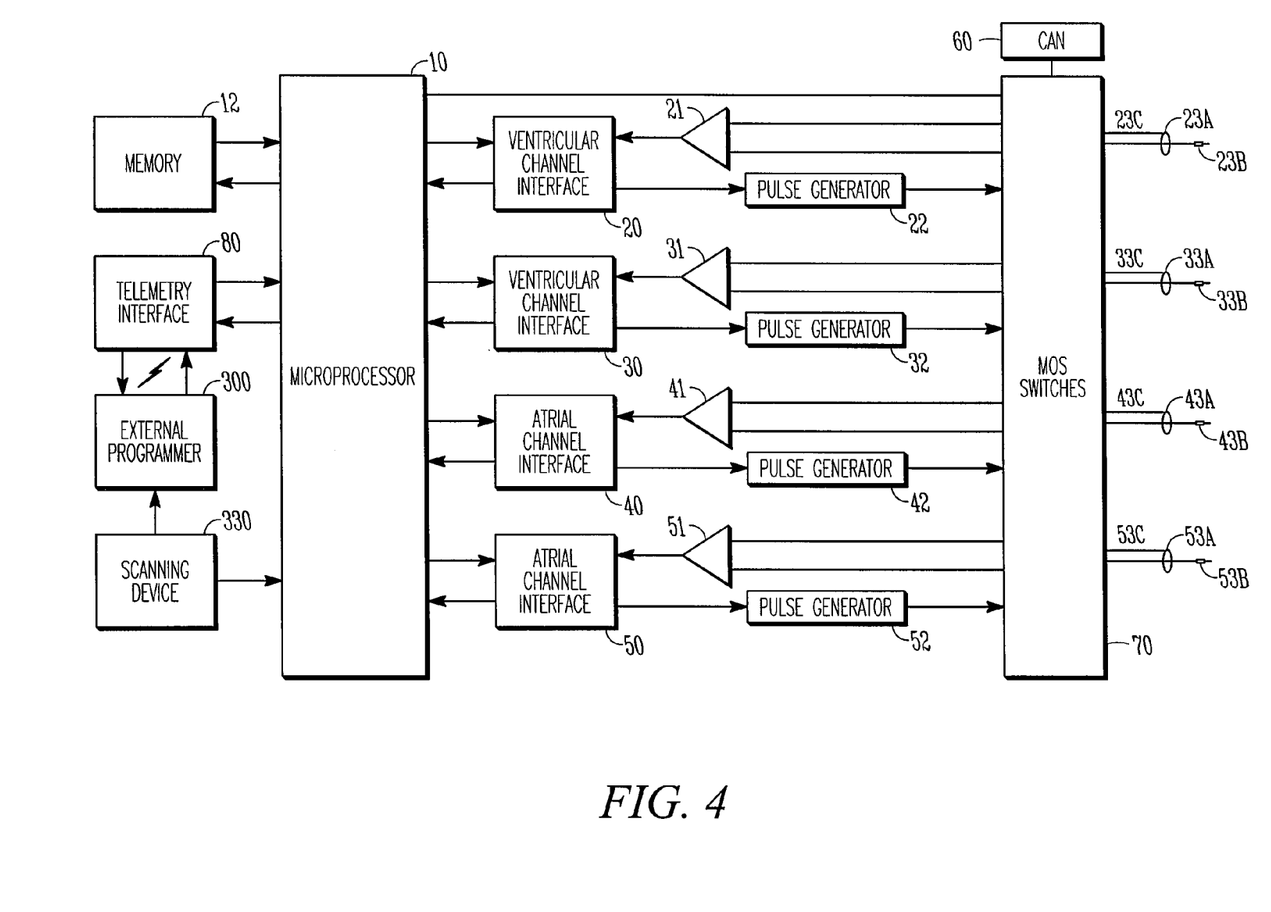
FIG. 4 is a system diagram of system components for diagnosing abnormal electro-mechanical coupling and delivering cardiac resynchronization therapy.

The following is a description of exemplary hardware components used for practicing the present invention. A block diagram of an implantable cardiac rhythm management device or pulse generator having multiple sensing and pacing channels is shown in FIG. 4. Pacing of the heart with an implanted device involves excitatory electrical stimulation of the heart by the delivery of pacing pulses to an electrode in electrical contact with the myocardium. The device is usually implanted subcutaneously on the patient's chest, and is connected to electrodes by leads threaded through the vessels of the upper venous system into the heart. An electrode can be incorporated into a sensing channel that generates an electrogram signal representing cardiac electrical activity at the electrode site and/or incorporated into a pacing channel for delivering pacing pulses to the site.

The controller of the device in FIG. 4 is made up of a microprocessor 10 communicating with a memory 12 via a bidirectional data bus, where the memory 12 typically comprises a ROM (read-only memory) and/or a RAM (random-access memory). The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to the code executed by a microprocessor. The controller is capable of operating the pacemaker in a number of programmed modes where a programmed mode defines how pacing pulses are output in response to sensed events and expiration of time intervals.

A telemetry interface 80 is provided for communicating with an external programmer 300. The external programmer is a computerized device with an associated display and input means that can interrogate the pacemaker and receive stored data as well as directly adjust the operating parameters of the pacemaker. As described below, in certain embodiments of a system for setting pacing parameters, the external programmer may be utilized for computing optimal pacing parameters from data received from the implantable device over the telemetry link which can then be set automatically or presented to a clinician in the form of recommendations. A scanning device 330 (e.g., an echocardiography device) is also provided for determining mechanical delays in the ventricles. The scanning device may be interfaced to the external programmer and/or wirelessly linked to the implantable device. Scanning data generated by the scanning device may be used by the processing device (e.g., either the external programmer or the implantable device controller) to determine mechanical delays and compute optimum pacing parameters.

The embodiment shown in FIG. 4 has four sensing/pacing channels, where a pacing channel is made up of a pulse generator connected to an electrode while a sensing channel is made up of the sense amplifier connected to an electrode. A MOS switching network 70 controlled by the microprocessor is used to switch the electrodes from the input of a sense amplifier to the output of a pulse generator. The switching network 70 also allows the sensing and pacing channels to be configured by the controller with different combinations of the available electrodes. The channels may be configured as either atrial or ventricular channels allowing the device to deliver conventional ventricular single-site pacing with or without atrial tracking, biventricular pacing, or multi-site pacing of a single chamber. In an example configuration, a left atrial sensing/pacing channel includes ring electrode 53a and tip electrode 53b of bipolar lead 53c, sense amplifier 51, pulse generator 52, and a channel interface 50, and a right atrial sensing/pacing channel includes ring electrode 43a and tip electrode 43b of bipolar lead 43c, sense amplifier 41, pulse generator 42, and a channel interface 40. A right ventricular sensing/pacing channel includes ring electrode 23a and tip electrode 23b of bipolar lead 23c, sense amplifier 21, pulse generator 22, and a channel interface 20, and a left ventricular sensing/pacing channel includes ring electrode 33a and tip electrode 33b of bipolar lead 33c, sense amplifier 31, pulse generator 32, and a channel interface 30. The channel interfaces communicate bi-directionally with a port of microprocessor 10 and include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. In this embodiment, the device is equipped with bipolar leads that include two electrodes which are used for outputting a pacing pulse and/or sensing intrinsic activity. Other embodiments may employ unipolar leads with single electrodes for sensing and pacing. The switching network 70 may configure a channel for unipolar sensing or pacing by referencing an electrode of a unipolar or bipolar lead with the device housing or can 60.

The controller controls the overall operation of the device in accordance with programmed instructions stored in memory. The controller interprets electrogram signals from the sensing channels and controls the delivery of paces in accordance with a pacing mode. The sensing circuitry of the device generates atrial and ventricular electrogram signals from the voltages sensed by the electrodes of a particular channel. An electrogram is analogous to a surface EKG and indicates the time course and amplitude of cardiac depolarization and repolarization that occurs during either an intrinsic or paced beat. When an electrogram signal in an atrial or ventricular sensing channel exceeds a specified threshold, the controller detects an atrial or ventricular sense, respectively, which pacing algorithms may employ to trigger or inhibit pacing.

2. Exemplary Implementation

Figure 5:
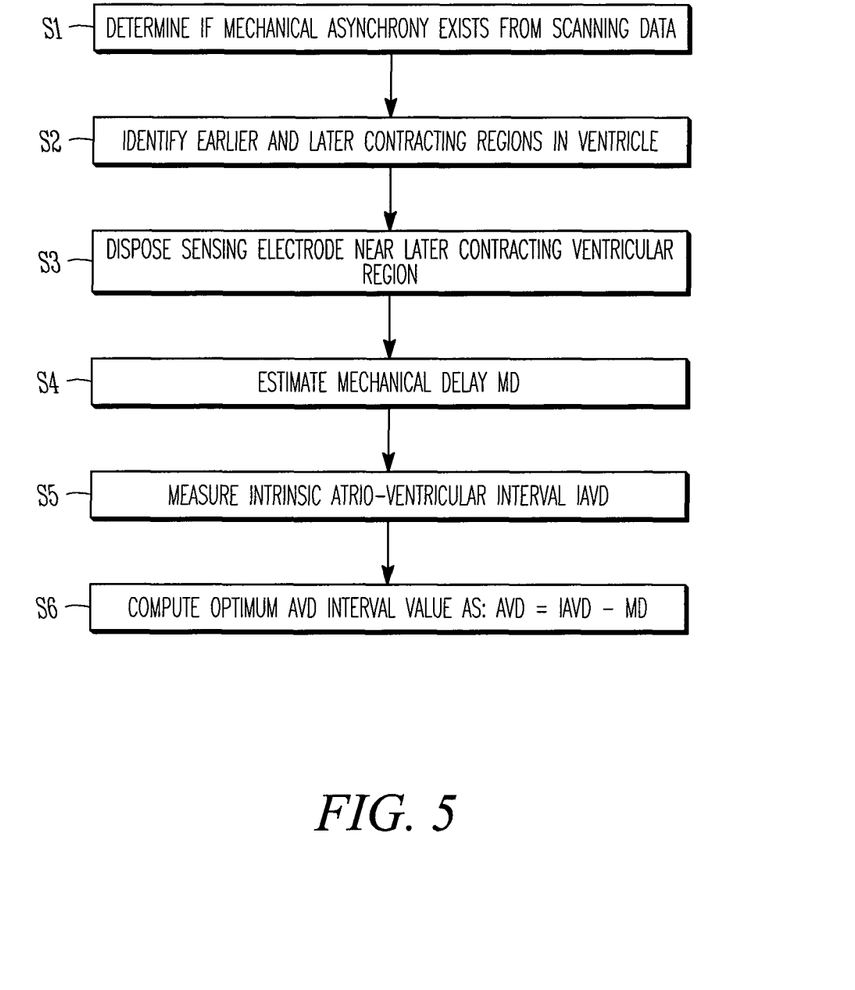
FIG. 5 is a flowchart showing an example of how the system may be used to diagnosis and treat a patient with ventricular asynchrony.

FIG. 5 is a flowchart showing an example of how the system components described above may be used to diagnosis and treat a patient with ventricular asynchrony due to abnormal cardiac electro-mechanical coupling. Mechanical asynchrony in the heart is determined from scanning data generated by the scanning device at step S1. If such asynchrony exists, an earlier contracting ventricular region and one or more later contracting regions are identified at step S2. A sensing electrode is then disposed near the later contracting region at step S3. Optionally, a sensing electrode may also be disposed near the earlier contracting region to determine if there is also any electrical delay and its extent. The sensing electrodes may be incorporated into the sensing channels of the implantable device. At step S4, the mechanical delay MD between mechanical activation of the earlier contracting site and the later contracting site is estimated from the scanning data by a processing device which may be the external programmer or the implantable device. Using data generated by an internal atrial sensing channel or from a surface EKG, the processing device at step S5 measures an intrinsic atrio-ventricular delay (IAVD) as the time between an atrial sense or pace and intrinsic electrical activation of the later contracting ventricular region. At step S6, the processing device then computes an atrio-ventricular delay interval (AVD) for delivering cardiac resynchronization pacing to the later contracting ventricular region in order to pre-excite that region as:

$$AVD=IAVD-MD.$$

The above example assumed that the patient had no electrical conduction abnormality in addition to abnormal electro-mechanical coupling. In another embodiment, sensing channels are provided for detecting electrical activity in both the earlier contracting and later contracting ventricular regions. The processing device is configured to determine the times at which the earlier and later contracting ventricular regions are electrically activated in order to determine which of the regions are the earlier and later electrically activated regions, to measure the mechanical delay between the time of contraction of the earlier contracting region and the later contracting region, and to measure the electrical delay between the times of activation of the earlier electrically activated region and the later electrically activated region. The processing device may then compute an atrio-ventricular delay interval (AVD) for delivering cardiac resynchronization pacing to the later contracting ventricular region in order to pre-excite that region as:

$$AVD=F(IAVD_1, IAVD_2)-MD$$

where $F(IAVD_1, IAVD_2)$ is a function of the intrinsic atrio-ventricular delay intervals to the earlier and later contracting ventricular regions, $IAVD_1$, and $IAVD_2$, respectively, computed in order to pre-excite the later contracting region in a manner which compensates for the electrical delay between the earlier activated region and the later activated region.

The techniques for computing resynchronization pacing parameters in order to compensate for mechanical delays as described above may be implemented in a number of different ways. In one embodiment, a system for computing the pacing parameters includes an external programmer which is interfaced to the scanning device and programmed determining the mechanical delays between ventricular regions based upon the scanning data generated by the scanning device. Intrinsic conduction data composed of or derived from electrogram signals generated by the sensing channels of an implantable cardiac resynchronization device during intrinsic beats (e.g., intrinsic atrio-ventricular interval or electrical delays between ventricular regions) may then be transmitted to the external programmer via a wireless telemetry link. The external programmer may then compute an appropriate resynchronization pacing parameters such as the AVD or BVO. In an automated system, the external programmer then automatically programs the implantable device with the computed optimum parameter values, while in a semi-automated system the external programmer presents the computed optimum values to a clinician in the form of a recommendation. An automated system may also be made up of the implantable device alone which collects intrinsic conduction data and scanning data transmitted to it wirelessly over the telemetry link, computes the optimum parameter values, and then sets the parameters accordingly. In another embodiment, which may be referred to as a manual system, the external programmer presents the collected intrinsic conduction and scanning data to a clinician who then programs the implantable device with parameters computed from the intrinsic conduction and scanning data by, for example, using a printed lookup table and procedure. Unless otherwise specified, references to a system for computing or setting pacing parameters throughout this document should be taken to include any of the automated, semi-automated, or manual systems just described.

Although the invention has bed described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A system for configuring cardiac resynchronization pacing, comprising:
   a scanning device for detecting mechanical contraction of a first ventricular region and a second ventricular region during non-paced ventricular beat;
   a processing device interfaced to the scanning device, wherein the processing device is configured to compute a mechanical delay (MD) as the difference between the times at which the first and second ventricular regions mechanically contract during the non-paced ventricular beat and determine which of the regions is the earlier contracting region and the later contracting region;
   sensing channels for detecting electrical activity in an atrium and the later contracting ventricular region, and wherein the processing device is further configured to measure an intrinsic atrio-ventricular delay (IAVD) as the time between an atrial sense or pace and intrinsic electrical activation of the later contracting ventricular region; and,
   wherein the processing device is further configured to compute an atrio-ventricular delay interval (AVD) for delivering cardiac resynchronization pacing to the later contracting ventricular region in order to pre-excite that region as:

AVD=IAVD−MD.

2. The system of claim 1 further comprising:
   sensing channels for detecting electrical activity in both the first and second ventricular regions; and,
   wherein the processing device is configured to determine the times at which the earlier and later contracting ventricular regions are electrically activated in order to determine which of the earlier and later mechanically contracting regions are the earlier and later electrically activated regions.

3. The system of claim 2 wherein the processing device is further configured to measure the mechanical delay between the time of contraction of the earlier contracting region and the later contracting region and to measure the electrical delay between the times of activation of the earlier electrically activated region and the later electrically activated region.

4. The system of claim 3 wherein the processing device is further configured to compute an atrio-ventricular delay interval (AVD) for delivering cardiac resynchronization pacing to the later contracting ventricular region in order to pre-excite that region as:

AVD=$F$(IAVD$_1$, IAVD$_2$)−MD where F(IAVD$_1$, IAVD$_2$) is a function of the intrinsic atrio-ventricular delay intervals to the earlier and later contracting ventricular regions, IAVD$_1$, and IAVD$_2$, respectively, computed in order to pre-excite the later contracting region in a manner which compensates for the electrical delay between the earlier activated region and the later activated region.

5. The system of claim 1 further comprising an implantable device equipped with sensing channels and pacing channels for delivering resynchronization pacing.

6. The system of claim 5 wherein the processing device is an external programmer.

7. The system of claim 5 wherein the processing device is a controller of the implantable device.

8. The system of claim 1 wherein the scanning device is an echocardiography device.

9. The system of claim 1 wherein the atrial sensing channel is a surface EKG device.

10. A method, comprising:
    detecting mechanical contraction of a first ventricular region and a second ventricular region during a non-paced ventricular beat;
    computing a mechanical delay (MD) as the difference between the times at which the first and second ventricular regions mechanically contract during the non-paced ventricular beat and determining which of the regions is the earlier contracting region and the later contracting region;
    detecting electrical activity in an atrium and the later contracting ventricular region, and measuring an intrinsic atrio-ventricular delay (IAVD) as the time between an atrial sense or pace and intrinsic electrical activation of the later contracting ventricular region; and,
    computing an atrio-ventricular delay interval (AVD) for delivering cardiac resynchronization pacing to the later contracting ventricular region in order to pre-excite that region as:

AVD=IAVD−MD.

11. The method of claim 10 further comprising:
    detecting electrical activity in both the first and second ventricular regions; and,
    determining the times at which the earlier and later contracting ventricular regions are electrically activated in order to determine which of the earlier and later mechanically contracting regions are the earlier and later electrically activated regions.

12. The method of claim 11 further comprising measuring the mechanical delay between the time of contraction of the earlier contracting region and the later contracting region and measuring the electrical delay between the times of activation of the earlier electrically activated region and the later electrically activated region.

13. The method of claim 12 further comprising computing an atrio-ventricular delay interval (AVD) for delivering cardiac resynchronization pacing to the later contracting ventricular region in order to pre-excite that region as:

$$AVD = F(IAVD_1, IAVD_2) - MD$$

where $F(IAVD_1, IAVD_2)$ is a function of the intrinsic atrio-ventricular delay intervals to the earlier and later contracting ventricular regions, $IAVD_1$, and $IAVD_2$, respectively, computed in order to pre-excite the later contracting region in a manner which compensates for the electrical delay between the earlier activated region and the later activated region.

* * * * *